United States Patent [19]
Guymer

[11] 3,981,584
[45] Sept. 21, 1976

[54] PREDICTION OF ENGINE FAILURE BY EXAMINATION OF PARTICLE SIZE DISTRIBUTION OF METAL PARTICLES IN LUBRICANT

[75] Inventor: Jon Anthony Guymer, Beaumaris, Australia

[73] Assignee: Mobil Oil Corporation, New York, N.Y.

[22] Filed: Dec. 23, 1974

[21] Appl. No.: 535,762

[30] Foreign Application Priority Data
June 13, 1974 Australia.............................. 7878/74

[52] U.S. Cl................................... 356/70; 356/86; 356/102
[51] Int. Cl.² ................. G01N 33/28; G01N 15/02
[58] Field of Search........................ 356/70, 86, 102

[56] References Cited
UNITED STATES PATENTS
| | | | |
|---|---|---|---|
| 3,526,127 | 9/1970 | Sarkis .................................... | 356/70 |
| 3,709,614 | 1/1973 | Hayakawa........................... | 356/102 |

OTHER PUBLICATIONS
"A Method . . . Wear Particle . . . Oil"; Seifert et al.; Wear, 21 (1972) pp. 27–42.
The Particles of Wear; Scientific American; May 1974; Scott et al. pp. 88–89.

Primary Examiner—Vincent P. McGraw
Attorney, Agent, or Firm—Charles A. Huggett; Raymond W. Barclay; Thomas S. Szatkowski

[57] ABSTRACT

Method for predicting incipient failure of a lubricated engine by removing a sample of the liquid lubricant employed after the same has been in contact with the moving metal surfaces of the engine. The metal wear particles contained in the lubricant are then separated into at least three predetermined size ranges by passage through membranes having pore openings corresponding in size to such predetermined size. Each of the fractions so separated is analyzed for a selected metal contaminant, such as iron, and the content of such metal contaminant is plotted against the particle size thereof. The likelihood of mechanical failure is determined from the shape of the resulting graph, with a preponderance of large metal contaminant particles being indicative of incipient engine failure.

6 Claims, 2 Drawing Figures

PREDICTION OF ENGINE FAILURE BY EXAMINATION OF PARTICLE SIZE DISTRIBUTION OF METAL PARTICLES IN LUBRICANT

BACKGROUND OF THE INVENTION

1. Field of the Invention.

This invention is concerned with a method for forecasting engine failure from particle size distribution of metal contaminant contained in the lubricant used in said engine.

2. Description of the Prior Art.

Wear at the interface between moving parts is a normal characteristic of machine operation. The kind and the rate of wear depend on the machine. Lubrication is normally provided between moving surfaces to minimize the wear. During operation millions of minute wear particles enter the lubricating oil. The particles range in size from several microns to a small fraction of micron, for example 20 millimicrons.

It has long been recognized that a knowledge of the quantity and of the rate of increase in the quantity of foreign material, particularly iron, in the lubricating oil of an engine can give valuable insight into the condition of the engine. Because the quantity of such material is extremely small, for example a few parts per million in the oil of a typical engine in good condition, it has been necessary to resort to sophisticated techniques to analyze the lubricating oil.

If oil containing these particles is observed under a high-powered transmitted-light microscope, only the largest particles can be seen. Nor is the situation improved by resorting to a microscope employing phase contrast or other interference techniques. The basic problem is that most of the particles range in size from a wavelength to a small fraction of a wavelength of light, and they do not disturb the phase or amplitude of the lightwave sufficiently to be seen.

Spectrographic techniques have been used relatively extensively to analyze lubricating oil, but even these techniques do not provide as much information as might be desired. For example, a spectrographic analysis is unable to distinguish between two samples containing foreign particles of very different average size but having the same total parts per million of contaminant.

The highly-stressed wearing parts of a machine are usually made of steel. Therefore, if the ferrous particles which collect in the oil are separated and examined, very significant information about the condition of the machine is capable of being obtained.

Heretofore, special magnetic techniques have been used which permit particles of iron or other magnetic material to be precipitated from an oil sample. In such system, the oil flows along a substrate in a magnetic field and large particles are deposited on one end of the substrate and small particles on the other. Particle sizes grade continuously in between. The substrate with the deposited particles affords a means of determining the condition of the engine and of predicting incipient failure.

The above described system, while effective, is time-consuming, expensive and, in some aspects, cumbersome. Thus, in addition to the special magnetic equipment requisite for carrying out the particle size distribution analyses, it is necessary, after the sample has been pumped through the system, to effect a washing and fixing cycle during which the oil remaining on the slide is removed and the particles are caused to adhere to the substrate.

SUMMARY OF THE INVENTION

In accordance with the present invention, there is provided an improved method of determining the failure condition of internal combustion engines. More particularly, the invention described herein is concerned with an improved method of ascertaining an impending failure in a component of an internal combustion engine, mechanical equipment or machine such as a gear box or the like.

Mechanical components of any apparatus are always subject to failure due to the mechanical stresses and strains imposed thereon. Such components may be subjected to normal or abnormal wear conditions or conditions of abnormal stress but heretofore the application of such abnormal conditions generally would go unnoticed until such time as the part actually failed in service.

The present invention is predicated on the finding that metal wear from mechanical components of equipment progresses from being relatively small particles to being relatively larger particles as the wear becomes more severe. When taken to the extreme, the metal wear from mechanical components which are about to fail or are in the state of being susceptible to failure tend to be relatively larger than other wear particles.

In one embodiment, the present invention provides a method of determining the wear condition of mechanical equipment which comprises the steps of passing a sample of lubricating oil taken from the equipment through various filters to separate wear particles of various sizes, determining the relative quantitative amounts of the particles of the various sizes and thereby determining the particle size distribution in the said sample to ascertain the state of wear of the equipment.

The method of the present invention is particularly applicable to forecasting mechanical failure in internal combustion engines such as jet engines, the forecasting being based on an analysis of the wear particles size distribution. The method of the invention is considered feasible for ascertaining the condition of equipment or apparatus wherein lubricated moving metal parts are involved including, for example in addition to jet engines, reciprocating engines and industrial machinery from which samples of lubricating oil can be taken.

A sample of the lubricating oil removed from the engine is, in accordance with the present method, passed through repeated filtrations through millipore membranes to obtain an indication of the particle size distribution. Generally, the metal wear particles contained in the lubricant are separated into at least three predetermined size ranges. Each of the fractions so separated is then analyzed, suitably by use of an emission spectrometer, for a selected metal contaminant such as iron. The content of the selected metal contaminant for each of the fractions is then plotted against the particle size thereof. From the shape of the resulting graph, the likelihood of mechanical failure in the engine can be determined.

DESCRIPTION OF SPECIFIC EMBODIMENTS

The following example will serve to illustrate the method of the invention without limiting the same:

Approximately 5 gram of lubricating oil sample, removed from an engine, is thoroughly shaken and passed through a 1.2 micron millipore membrane under vacuum conditions.

The filtrate is then transferred to a labelled container and subsequently analyzed in duplicate for metal, i.e. iron content. The result of the analysis provides the concentration of metal in the sample below 1.2 micron size.

Approximately 5 gram of the oil sample is again thoroughly shaken and passed this time through a millipore membrane of 0.3 micron under vacuum conditions. The filtrate is subsequently analyzed to provide an indication of metal, i.e. iron, concentration below 0.3 micron.

The results are compared to the measurement of the total amount of free iron in the samples and the results are plotted on a graph to indicate the relative amounts of particles of various sizes — that is below 0.3 microns, between 0.3 and 1.2 microns and above 1.2 microns. The following table provides a summary of the results obtained from a number of sample tests.

| Engine No. | Sample No. | Total Fe | Below 1.2μ | Below 0.3μ | |
|---|---|---|---|---|---|
| 1 | 1 | 5 | 3 | 1 | low iron content but high proportion of large particles indicated impending failure of component subsequently confirmed sheared constant speed drive shaft |
| 2 | 1 | 8 | 8 | 6 | Engine operated normally |
|   | 2 | 6 | 6 | 5 |   |
| 3 | 1 | 16 | 15 | 14 | High iron content but low proportion of large particles. Engine operated normally |
| 4 | 1 | 24 | 16 | 9 | High proportion of large particles indicate falure imminent - subsequently confirmed. |
| 5 | 1 | 5 | 4 | 1 | low iron content but high proportion of large particles indicates failure of component in oil circuit-subsequently confirmed. |
|   | 2 | 6 | 5 | 2 |   |
|   | 3 | 5 | 3 | 1 |   |
| 6 | 1 | 22 | 20 | 16 | Sample taken from engine incorporating gear-box particle distribution indicates normal wear. |
| 7 | 1 | 8 | 7 | 6 | Indicates failure unlikely - Engine continued to operate without failure thus avoiding unnecesssary removal |
|   | 2 | 9 | 9 | 14 |   |
|   | 3 | 15 | 8 | 13 |   |
| 8 | 1 | 7 | 6 | 3 | Indicates unlikely to fail in immediate |
|   | 2 | 5 | 4 | 2 |   |

-continued

| Engine No. | Sample No. | Total Fe | Below 1.2μ | Below 0.3μ | |
|---|---|---|---|---|---|
|   | 3 | 16 | 15 | 14 | future. |
|   | 4 | 14 | 13 | 12 |   |
| 9 | 1 | 10 | 9 | 5 | Change in pattern indicates change in wear rates and high iron in later samples shows failure imminent-subsequently confirmed |
|   | 2 | 14 | 12 | 7 |   |
|   | 3 | 18 | 14 | 6 |   |
|   | 4 | 17 | 11 | 2 |   |

Figure 1:
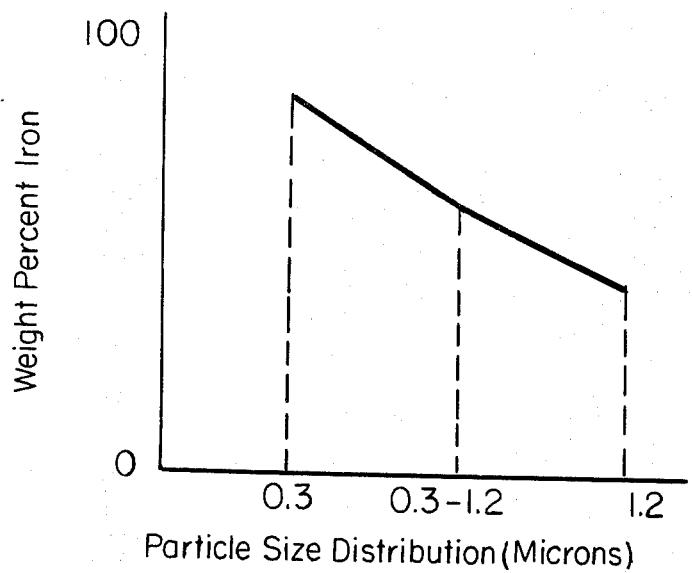
FIG. 1 is a graph showing the relationship between the amount of iron in a test sample and particle size distribution in such sample.

When the results as indicated above are plotted on a bar chart which is then developed into a "graph" the graph appears as that shown in FIG. 1.

Figure 2:
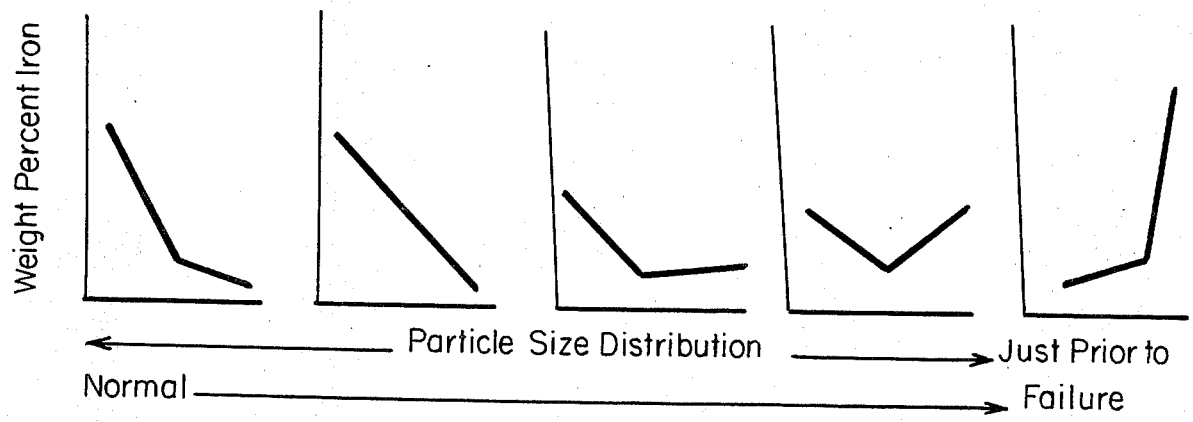
FIG. 2 depicts a family of graphs in which the relationship of iron content and particle size distribution is shown progressing from normal wear to incipient failure.

The present invention shows that the progression from normal wear to wear indicating impending failure can be illustrated by a family of graphs of the type shown in FIG. 2. Referring more particularly to this Figure, it will be seen, proceeding from left to right, that the results show such a progression from the engines with normal wear to those about to fail.

It will be clearly seen from the results that when the relative amount of the larger sized particles increases relative to the total amount of particles then prediction can be made that the engine is approaching a failure situation. The results confirm that when normal wear is taking place wear particles are predominantly small and when serious wear is occurring larger particles are generated which serve as an indication of impending component failure. It should be noted that large amounts of iron particles in the oil samples — that is greater than 20 ppm — do not necessarily indicate a high degree of wear which will result in early failure of engine components. The results show that even when the concentration of iron particles is relatively low, e.g. 5 parts per million, the size range distribution can still indicate impending engine failure.

The methods of the present invention are relatively insensitive to the length of time oil has been in the engine under consideration so that relatively frequent oil changes and high oil consumption with attendant oil dilution do not effect the results of the tests.

While the invention has been described utilizing procedures for determining the amount of particle in the size ranges of below 0.3 micron, between 0.3 and 1.2 micron, and greater than 1.2 micron, it will be appreciated that these size ranges may be varied according to particular engines investigated and conditions of service. Thus, it is envisaged that the lower size range may be of the order of between 0.1 and 0.8 micron and the upper size range may be of particles of sizes greater than between 1 and 5 microns, with the intermediate size range being between the selected lower size and upper size of the examined particles. Naturally, as millipore membrane filters are readily available in standard sizes, then these sizes are preferred for economy and convenience.

It is to be understood that the foregoing description is merely illustrative of preferred embodiments of the invention of which many variations may be made by those skilled in the art within the scope of the following claims without departing from the spirit thereof.

I claim:

1. A method for predicting incipient failure of an apparatus having moving metal surfaces, which surfaces are wetted with a liquid lubricant which comprises separating the metal wear particles contained in a sample of said lubricant into at least three predetermined size ranges by passage through membranes having pore openings corresponding in size to said predetermined size, analyzing each of the fractions so separated for a selected metal contaminant, plotting the content of said metal contaminant for each of said fractions against the particle size thereof and determining the likelihood of mechanical failure in said apparatus from the shape of the resulting graph.

2. The method of claim 1 wherein said apparatus is an engine.

3. The method of claim 1 wherein said apparatus is a jet engine.

4. The method of claim 1 wherein said metal contaminant is iron.

5. The method of claim 1 wherein said predetermined size ranges include a lower size range of between 0.1 and 0.8 micron, an upper size range between 1 and 5 mircons and an intermediate size range between the selected lower size and upper size range.

6. The method of claim 1 wherein said predetermined size ranges include particles below 0.3 micron, between 0.3 and 1.2 micron and greater than 1.2 micron.

* * * * *

UNITED STATES PATENT AND TRADEMARK OFFICE
CERTIFICATE OF CORRECTION

PATENT NO. : 3,981,584
DATED : September 21, 1976
INVENTOR(S) : JON ANTHONY GUYMER It is certified that error appears in the above-identified patent and that said Letters Patent are hereby corrected as shown below:

Column 1, line 22     "of micron" should be --of a micron--

Column 5, line 2      "the metal wear particles" should be --the particles--.

Column 5, line 7      "separated for" should be --separated by use of an emission spectrometer for--.

Signed and Sealed this

Twenty-second Day of February 1977

[SEAL]

Attest:

RUTH C. MASON
*Attesting Officer*

C. MARSHALL DANN
*Commissioner of Patents and Trademarks*